(12) United States Patent
Li et al.

(10) Patent No.: US 8,798,746 B2
(45) Date of Patent: Aug. 5, 2014

(54) AUTOMATIC MECHANICAL ALTERNANS DETECTION

(75) Inventors: Dan Li, Shoreview, MN (US); Allan C. Shuros, St. Paul, MN (US); Arjun Sharma, St. Paul, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 176 days.

(21) Appl. No.: 13/007,107

(22) Filed: Jan. 14, 2011

(65) Prior Publication Data

US 2011/0178565 A1 Jul. 21, 2011

Related U.S. Application Data

(60) Provisional application No. 61/295,432, filed on Jan. 15, 2010.

(51) Int. Cl.
*A61N 1/365* (2006.01)

(52) U.S. Cl.
USPC .......................................................... 607/17

(58) Field of Classification Search
USPC .................. 607/2, 3, 14–17; 600/510–516
See application file for complete search history.

(56) References Cited

U.S. PATENT DOCUMENTS

| | | | |
|---|---|---|---|
| 5,921,940 A | 7/1999 | Verrier et al. | |
| 6,666,826 B2 | 12/2003 | Salo et al. | |
| 6,915,157 B2 | 7/2005 | Bennett et al. | |
| 7,039,462 B2 | 5/2006 | Pastore et al. | |
| 7,113,825 B2 | 9/2006 | Pastore et al. | |
| 7,225,014 B1 * | 5/2007 | Province | 600/516 |
| 7,257,443 B2 | 8/2007 | Pastore et al. | |
| 7,366,569 B2 | 4/2008 | Belalcazar | |
| 7,620,448 B1 | 11/2009 | Farazi et al. | |
| 7,697,978 B1 | 4/2010 | Farazi | |
| 2003/0097158 A1 | 5/2003 | Belalcazar | |
| 2003/0158584 A1 * | 8/2003 | Cates et al. | 607/2 |
| 2004/0162497 A1 | 8/2004 | Bennett et al. | |
| 2006/0020294 A1 | 1/2006 | Brockway et al. | |
| 2006/0116596 A1 | 6/2006 | Zhou et al. | |
| 2006/0122522 A1 | 6/2006 | Chavan et al. | |
| 2008/0269627 A1 | 10/2008 | Cho et al. | |
| 2009/0076345 A1 | 3/2009 | Manicka et al. | |
| 2009/0076559 A1 | 3/2009 | Libbus et al. | |
| 2009/0143692 A1 | 6/2009 | Brockway et al. | |
| 2009/0177110 A1 | 7/2009 | Lyden et al. | |

(Continued)

FOREIGN PATENT DOCUMENTS

WO WO-2011/088337 A1 7/2011

OTHER PUBLICATIONS

International Application Serial No. PCT/US2011/021324, International Search Report mailed Mar. 24, 2011, 4 pgs.

(Continued)

*Primary Examiner* — Rex R Holmes
(74) *Attorney, Agent, or Firm* — Schwegman, Lundberg & Woessner, P.A.

(57) ABSTRACT

This document discusses, among other things, a cardiac mechanical alternans (MA) detector circuit. In an example, the mechanical alternans detector circuit is configured to determine a mechanical alternans (MA) condition. In an example, the MA detector circuit can include a physiologic impedance input configured to receive physiologic information indicative of mechanical alternans. In an example, the MA detector circuit can include an intravascular pressure input configured to receive physiologic information indicative of mechanical alternans.

11 Claims, 8 Drawing Sheets

(56) References Cited

U.S. PATENT DOCUMENTS

| | | |
|---|---|---|
| 2009/0275848 A1 | 11/2009 | Brockway et al. |
| 2009/0326595 A1 | 12/2009 | Brockway et al. |
| 2010/0049270 A1 | 2/2010 | Pastore et al. |
| 2010/0179610 A1 | 7/2010 | Farazi et al. |
| 2010/0305648 A1 | 12/2010 | Arcot-krishnamurthy et al. |
| 2011/0004075 A1 | 1/2011 | Stahmann et al. |
| 2011/0201952 A1* | 8/2011 | Cho et al. .................. 600/510 |

OTHER PUBLICATIONS

International Application Serial No. PCT/US2011/021324, Written Opinion mailed Mar. 24, 2011, 7 pgs.

International Application Serial No. PCT/US2011/021324, International Preliminary Report on Patentability mailed Jul. 26, 2012, 8 pgs.

Hirashiki, A., et al., "Prognostic value of pacing-induced mechanical alternans in patients with mild-to-moderate idiopathic dilated cardiomyopathy in sinus rhythm.", J Am Coll Cardiol. Apr. 4, 2006;47(7):, 1382-9.

Kodama, M., et al., "Linkage between mechanical and electrical alternans in patients with chronic heart failure", J Cardiovasc Electrophysiol., 15(3), (Mar. 2004), 295-9.

Kodama, M., et al., "Ventricular fibrillation in two cases with dilated cardiomyopathy and mechanical alternans.", Pacing Clin Electrophysiol., 28(12), (Dec. 2005), 1347-9.

Kodama, Makoto, et al., "Mechanical alternans in patients with chronic heart failure.", J Card Fail., 7(2), (Jun. 2001), 138-45.

Valzania, Cinzia, "Electromechanical effects and optimization modalities of cardiac resynchronization therapy", Karolinska Institutet, Department of Medicine, Stockholm 2009, 54 pgs.

* cited by examiner

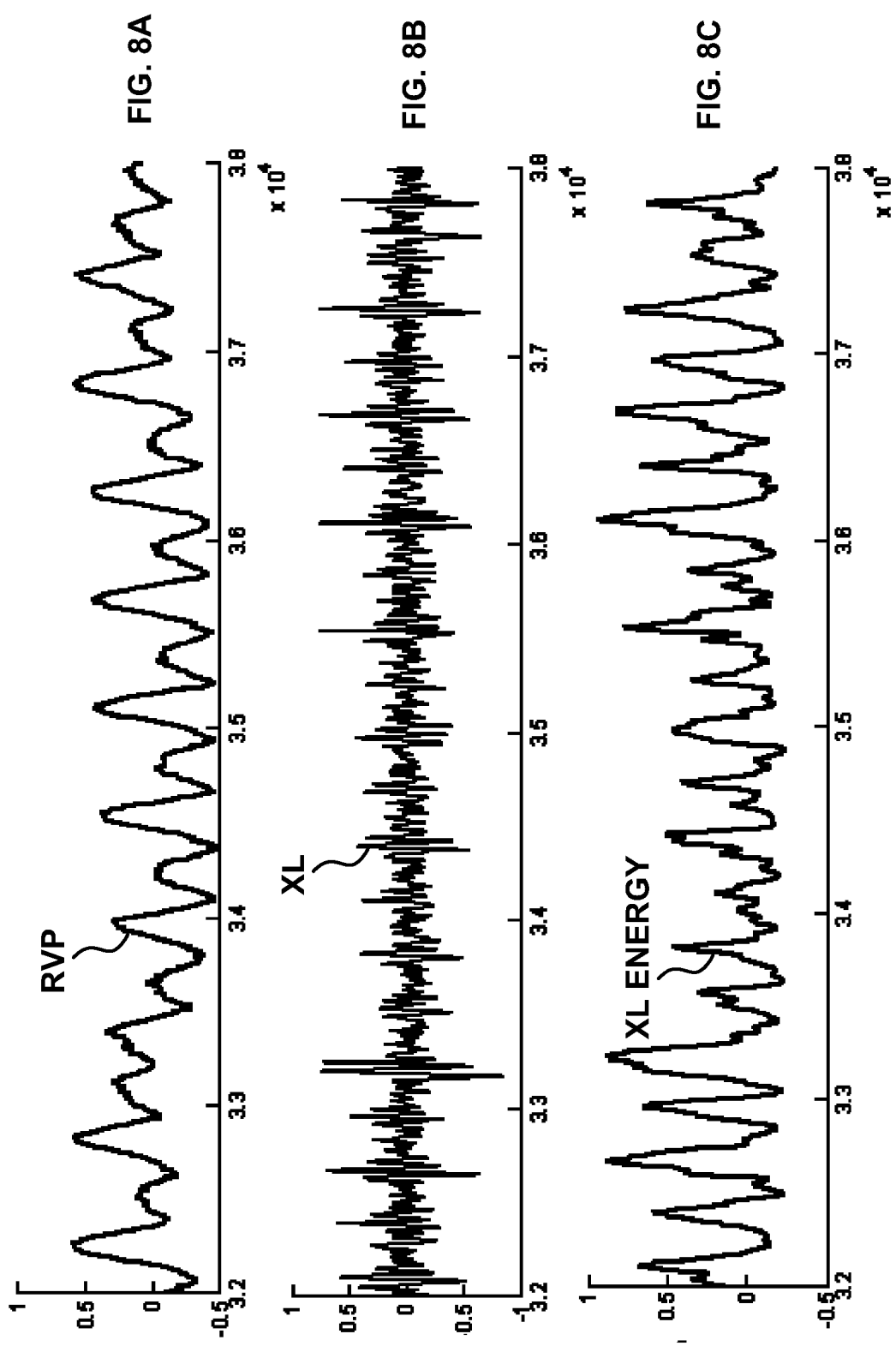

AUTOMATIC MECHANICAL ALTERNANS DETECTION

CLAIM OF PRIORITY

This patent application claims the benefit of priority, under 35 U.S.C. Section 119(e), to Li, et al., U.S. Provisional Patent Application Ser. No. 61/295,432, entitled "Automatic Mechanical Alternans Detection," filed on Jan. 15, 2010 which is hereby incorporated by reference herein in its entirety.

BACKGROUND

A heart can be considered the center of a circulatory system within a body. For example, the heart can take deoxygenated blood from elsewhere in the body and provide it to the lungs to be oxygenated. The heart can then supply the oxygenated blood from the lungs to other parts of the body. In a healthy heart, each chamber can contract in a coordinated fashion, such as to provide adequate circulation of oxygenated blood and nutrients to sustain the body.

The heart can be affected by a variety of physical and electrical abnormalities. Physical abnormalities can include, among other things, enlarging of the heart, sometimes associated with ischemia. Electrical abnormalities can include, among other things, various arrhythmias, such as due to prior infarcts, congenital defects, aging, or one or more other factors. These various abnormalities can be associated with one or more underlying acute or chronic diseases. For example, congestive or chronic heart failure can result in both physical and electrical abnormalities, such as those described above. In certain cases, a patient suffering from heart failure can experience life-threatening arrhythmias, such as a ventricular tachyarrhythmia, either caused by the heart failure condition itself or due to one or more other causes.

OVERVIEW

The present inventors have recognized, among other things, that mechanical alternans (MA) may be a better predictor of worsening heart function (e.g., increasing left ventricular dysfunction) than other predictors, such as using a measurement of a left ventricular ejection fraction (LVEF) or measurement of a level of plasma brain natriuretic peptide (BNP). Information provided by an MA detector circuit can be used to aid the patient or caregiver in tracking the status of a disease such as congestive or chronic heart failure.

This document discusses, among other things, a cardiac MA detector circuit configured to determine an MA condition. In certain examples, the MA detector circuit can include a physiologic impedance input configured to receive physiologic information indicative of MA. In certain examples, the MA detector circuit can include an intravascular pressure input configured to receive physiologic information indicative of MA. In certain examples, the MA detector circuit can be included as a part, component, or portion of an implantable medical device.

In certain examples, information provided by the MA detector circuit can be used by the implantable medical device to automatically alter, initiate, or discontinue one or more therapies, such as a cardiac resynchronization therapy.

In Example 1, an apparatus can include a cardiac mechanical alternans (MA) detector circuit comprising a physiologic impedance input configured to receive physiologic information indicative of mechanical alternans, an intravascular pressure input configured to receive physiologic information indicative of mechanical alternans, a mechanical input configured to receive physiologic cardiac vibration information indicative of mechanical alternans. In this example the MA detector circuit can be configured to determine a mechanical alternans (MA) condition at least in part using the physiologic information received by the physiologic impedance input, the intravascular pressure input, and the mechanical input.

In Example 2, some or all of the subject matter of Example 1 optionally includes a therapy circuit configured to provide at least one of a high output pacing therapy, an intermittent pacing therapy, a bradyarrhythmia therapy, a cardiac resynchronization therapy, or an anti-tachyarrhythmia therapy. In this example, the therapy circuit can be configured to adjust a therapy parameter in response to information about the MA condition provided by the MA detector circuit, and the MA detector circuit can be configured to classify the mechanical alternans as one of a discordant MA condition, a concordant MA condition, or an intermediate condition between the concordant and discordant conditions.

In Example 3 an apparatus can include a cardiac mechanical alternans (MA) detector circuit comprising a physiologic impedance input configured to receive physiologic information indicative of mechanical alternans, an intravascular pressure input configured to receive physiologic information indicative of mechanical alternans. In this example, the MA detector circuit can be configured to determine a mechanical alternans (MA) condition at least in part using the physiologic information received by the physiologic impedance input and the intravascular pressure input.

In Example 4, some or all of the subject matter of any one or more of Examples 1-3 optionally includes an MA detector circuit comprising a mechanical input configured to receive physiologic cardiac vibration information indicative of mechanical alternans, the MA detector circuit configured to determine an MA condition at least in part using the physiologic cardiac vibration information.

In Example 5, some or all of the subject matter of Example 4 optionally includes a mechanical receiver configured to receive cardiac vibration information indicative of mechanical such as including S3 heart sound. In this example, the MA detector circuit can be configured to determine the MA condition at least in part by using at least one of an energy or a power of the S3 heart sound.

In Example 6, some or all of the subject matter of any one or more of Examples 1-5 optionally includes an intravascular pressure sensor sized and shaped to be located intravascularly within or near at least one of a pulmonary artery, a coronary sinus, or a coronary vein. In this example, the pressure sensor can be configured to provide physiologic pressure information indicative of mechanical alternans to the intravascular pressure input.

In Example 7, some or all of the subject matter of Example 6 optionally includes an intravascular pressure sensor configured to wirelessly provide the physiologic pressure information to the intravascular pressure input, and wherein the intravascular pressure sensor is physically separate from the intravascular pressure input.

In Example 8, some or all of the subject matter of any one or more of Examples 1-7 optionally includes an MA detector circuit comprising a cardiac electrogram input configured to receive physiologic information obtained using a cardiac electrogram sensor, the MA detector circuit configured to determine at least one of an ischemic condition, a heart failure condition, an arrhythmic condition, an electrical alternans condition, or an autonomic balance condition using the physiologic information obtained using the cardiac electrogram sensor and the MA condition.

In Example 9, some or all of the subject matter of any one or more of Examples 1-8 optionally includes a therapy circuit configured to provide an electrostimulation to a heart. In this example, the MA detector circuit can be configured to determine the MA condition at least in part using the therapy circuit to provide the electrostimulation to the heart.

In Example 10, some or all of the subject matter of Example 9 optionally includes a therapy circuit configured to increase, such as in response to a command, at least one of a pacing amplitude or a pacing rate beyond a respective specified baseline pacing amplitude or a specified baseline pacing rate. In this example, the MA detector circuit can be configured to determine the MA condition at least in part using at least one of the pacing amplitude increase or the pacing rate increase.

In Example 11, some or all of the subject matter of any one or more of Examples 1-10 can include an MA detector circuit comprising a cardiac electrogram input configured to receive physiologic information obtained using an cardiac electrogram sensor. In this example, the MA detector circuit can be configured to at least one of inhibit or trigger a mechanical alternans determination using the physiologic information obtained using the electrogram sensor.

In Example 12, some or all of the subject matter of Example 11 optionally includes a cardiac electrogram input configured to receive physiologic information including an intrinsic heart rate. In this example, the MA detector circuit can be configured to determine the MA condition at least in part during an interval when the intrinsic heart rate exceeds a specified threshold.

In Example 13, some or all of the subject matter of any one or more Examples 1-12 optionally includes a therapy circuit configured to provide at least one of a high output pacing therapy, an intermittent pacing therapy, a bradyarrhythmia therapy, a cardiac resynchronization therapy, or an anti-tachyarrhythmia therapy. In this example, the therapy circuit can be configured to adjust a therapy parameter in response to information about the MA condition provided by the MA detector circuit. In this example, the MA detector circuit can be configured to classify the mechanical alternans as one of a discordant MA condition, a concordant MA condition, or an intermediate condition between the concordant and discordant conditions In Example 14, some or all of the subject matter of any one or more Examples 1-13 optionally includes an MA detector circuit configured to determine a duration of mechanical alternans.

In Example 15, some or all of the subject matter of any one or more Examples 1-14 optionally includes a physiologic impedance input configured to receive information about a left ventricular cardiac impedance, and an intravascular pressure input configured to receive information about an intravascular pressure at or near a right ventricle.

In Example 16, some or all of the subject matter of any one or more Examples 1-15 optionally includes a physiologic impedance input configured to receive information about at least one of a cross-chamber impedance between a left ventricle and a right ventricle, or between the left ventricle and a right atrium.

In Example 17, some or all of the subject matter of any one or more Examples 1-16 optionally includes at least one of a physiologic impedance input or intravascular pressure input configured to receive information corresponding to a strong heart contraction and information corresponding to a weak heart contraction. In this example, the MA detector circuit can be configured to calculate a relative indication of information corresponding to the strong heart contraction to information corresponding to the weak heart contraction.

In Example 18, some or all of the subject matter of any one or more Examples 1-17 optionally includes an MA detector configured to calculate a relative indication including a first value obtained using physiologic information corresponding to a first heart contraction divided by a second value obtained using physiologic information corresponding to a second heart contraction, where at least one of the first or second heart contractions is weak.

In Example 19, some or all of the subject matter of Example 18 optionally includes first and second values corresponding to respective first and second peak cardiac impedances.

In Example 20, some or all of the subject matter of Example 18 optionally includes first and second values corresponding to respective first and second peak intravascular pressures.

In Example 21, some or all of the subject matter of Example 18 optionally includes first and second values corresponding to at least one of respective first and second energies or respective first and second powers of at least a portion of the physiologic information corresponding to respective first and second heart contractions.

In Example 22, some or all of the subject matter of any one or more of Examples 1-21 optionally includes an MA detector circuit configured to calculate at least two relative indications corresponding to each of at least two different pairs of successive heart contractions, the pairs each including a respective strong contraction and a respective weak contraction. In this example, the MA detector circuit can be configured to calculate a central tendency of the at least two relative indications.

In Example 23, some or all of the subject matter of any one or more of Examples 1-22 optionally includes an MA detector circuit configured to calculate an indication of a spread between the at least two relative indications.

In Example 24, a method can include receiving physiologic impedance information indicative of mechanical alternans obtained using an ambulatory sensor, receiving physiologic intravascular pressure information indicative of mechanical alternans obtained using an ambulatory sensor, and using a signal processor circuit, determining a mechanical alternans (MA) condition at least in part using the physiologic impedance information and the intravascular pressure information and providing information about the MA condition to a user or automated process.

In Example 25, some or all of the subject matter of any one or more of Examples 1-24 optionally includes receiving cardiac vibration information indicative of mechanical alternans obtained using an mechanical sensor, and determining the MA condition at least in part using the cardiac vibration information.

In Example 26, some or all of the subject matter of any one or more of Examples 1-25 optionally includes receiving the intravascular pressure information from an intravascular pressure sensor sized and shaped to be located intravascularly within or near at least one of a pulmonary artery, a coronary sinus, or a coronary vein.

In Example 27, some or all of the subject matter of any one or more of Examples 1-26 optionally includes receiving cardiac electrogram information indicative of at least one of an ischemic condition, a heart failure condition, an arrhythmic condition, an electrical alternans condition, or an autonomic balance condition, and determining at least one of the ischemic condition, the heart failure condition, the arrhythmic condition, the electrical alternans condition, or the autonomic balance condition using the cardiac electrogram information and the MA condition.

In Example 28, some or all of the subject matter of any one or more of Examples 1-27 optionally includes providing an electrostimulation to a heart using a therapy circuit, and determining the MA condition at least in part using the electrostimulation.

In Example 29, some or all of the subject matter of Example 28 optionally includes receiving a command, and in response to the command, providing the electrostimulation including increasing at least one of a pacing amplitude or a pacing rate beyond a respective specified baseline pacing amplitude or a specified baseline pacing rate, and determining the MA condition using at least one of the increased pacing amplitude or the increased pacing rate.

In Example 30, some or all of the subject matter of any one or more of Examples 1-29 optionally includes receiving cardiac electrogram information and in response, at least one of inhibiting or triggering the determining the MA condition using the received cardiac electrogram information.

In Example 31, some or all of the subject matter of any one or more of Examples 1-30 optionally includes receiving cardiac electrogram information indicative of an intrinsic heart rate, comparing the received cardiac electrogram information with a specified threshold, and in response, determining the MA condition at least in part during an interval when the intrinsic heart rate exceeds the specified threshold.

In Example 32, some or all of the subject matter of any one or more of Examples 1-31 optionally includes determining a duration of the mechanical alternans.

In Example 33, some or all of the subject matter of any one or more of Examples 1-32 optionally includes providing at least one of a high output pacing therapy, an intermittent pacing therapy, a bradyarrhythmia therapy, a cardiac resynchronization therapy, or an anti-tachyarrhythmia therapy, and adjusting one or more therapy parameters in response to information about the MA condition. In this example, the determining the MA condition can include classifying the mechanical alternans as one of a discordant MA condition, a concordant MA condition, or an intermediate condition between the concordant and discordant conditions.

In Example 34, some or all of the subject matter of any one or more of Examples 1-33 optionally includes receiving the physiologic impedance information about a left ventricular cardiac impedance, and receiving information about an intravascular pressure at or near a right ventricle.

In Example 35, some or all of the subject matter of any one or more of Examples 1-34 optionally includes receiving information about at least one of a cross-chamber impedance between a left ventricle and a right ventricle, or between the left ventricle and a right atrium.

In Example 36, some or all of the subject matter of any one or more of Examples 1-37 optionally includes at least one of the receiving the physiologic impedance information or the receiving the intravascular pressure information including receiving information corresponding to a strong heart contraction and information corresponding to a heart contraction. In this example, the method can include calculating a relative indication of information corresponding to the strong heart contraction to information corresponding to the weak heart contraction, and determining the MA condition using the relative indication.

In Example 37, some or all of the subject matter of any one or more of Examples 1-36 optionally includes obtaining from at least one of the intravascular pressure information or the physiologic impedance information a first value corresponding to a first heart contraction, obtaining from at least one of the intravascular pressure information or the physiologic impedance information a second value corresponding to a second heart contraction, and calculating the relative indication including dividing the first value by the second value, where at least of the first or second heart contractions is weak.

In Example 38, some or all of the subject matter of Example 37 optionally includes deriving the first and second values including determining respective first and second peak cardiac impedances using the physiologic impedance information, such as where the first and second values are respectively the first and second peak cardiac impedances.

In Example 39, some or all of the subject matter of Example 37 optionally includes obtaining the first and second values including obtaining respective first and second peak intravascular pressures using the intravascular pressure information, and wherein the first and second values are respectively the first and second peak intravascular pressures.

In Example 40, some or all of the subject matter of Example 37 optionally includes obtaining the first and second values including determining at least one of respective first and second energies or respective first and second powers of at least a portion of the physiologic impedance information or the intravascular pressure information corresponding to the respective first and second heart contractions.

In Example 41, some or all of the subject matter of Example 37 optionally includes calculating at least two relative indications corresponding to each of at least two different pairs of successive heart contractions, the pairs each including a respective strong contraction and a respective weak contraction, and calculating a central tendency of the at least two relative indications, such as where the determining the MA condition includes using the central tendency.

In Example 42, some or all of the subject matter of Example 37 optionally includes calculating an indication of spread between the at least two relative indications, such as where the determining the MA condition includes using the indication of spread.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 8A-C include illustrative examples of plots of physiologic information including an intravascular pressure, raw mechanical sensor information, and processed mechanical sensor information.

DETAILED DESCRIPTION

Figure 1:
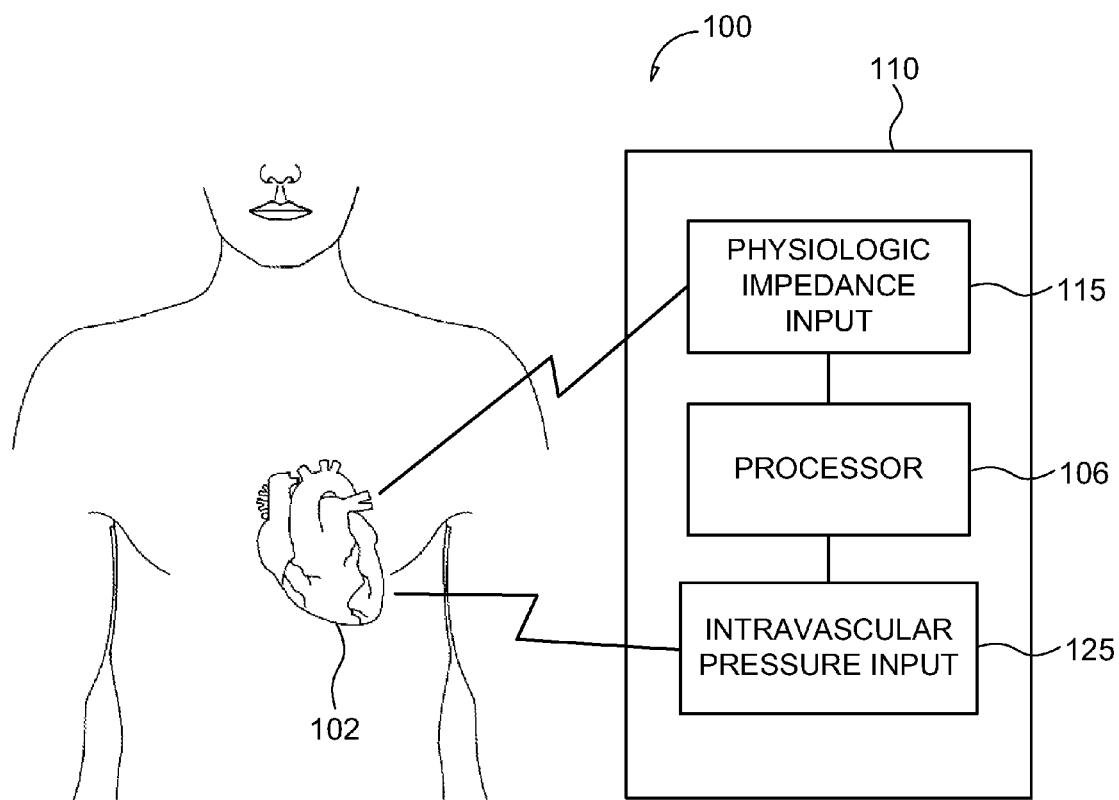
FIG. 1 illustrates generally an example of at least a portion of a system including cardiac MA detector circuit.

An implantable medical device can be used to monitor or treat one or more physical or electrical abnormalities of a heart. Certain symptoms, such as variation in the heart's mechanical pumping action, can be useful indicators of a disease status or a disease progression. For example, mechanical alternans (MA) can be described as a condition where successive mechanical contractions of a heart include alternating or varying degrees of forcefulness. In certain examples of MA, blood pressure in various portions of the heart can vary from one respective heart beat to another. The variation in blood pressure can be related to the degree of forcefulness of the mechanical contractions of the heart, such as including one or more relatively weaker contractions and one or more relatively stronger contractions. During MA, the heart contractions need not alternate between weaker or stronger contractions in a one-to-one manner. For example, MA can sometimes include short sequences of relatively weaker contractions followed by sequences of stronger contractions.

In some examples, MA can be localized such as to a specified region of the heart, such as a specific chamber. For example, in discordant MA, MA can occur in a left ventricle, but need not be occurring at the same time in a right ventricle. In other examples, MA can occur in both the left ventricle and the right ventricle at the same time, thus, the MA is concordant. The MA condition can also be intermediate, rather than strictly concordant or strictly discordant, such as where MA is occurring in more than one region, but a degree of variation is different depending on the region.

MA can be distinguished from electrical alternans, such as T-wave alternans ("TWA"). TWA can be described as a condition where an electrocardiogram or a cardiac electrogram signal includes alternating or varying amplitudes of electrical activity. For example, TWA can occur in the absence of MA, and can indicate a heightened risk of death from sudden cardiac arrest. It is believed that the type (e.g., concordant or discordant), presence, or duration of MA may be used such as to predict different underlying diseases or conditions as compared to using TWA.

The present inventors have also recognized, among other things, that information about the MA condition (e.g., the presence, duration, or type of MA) can be used, for example, such as to monitor or predict a progression of one or more diseases. In an example, left ventricular MA can correlate with a presence of congestive heart failure. In an example, a sustained interval of MA or intervals of increasing MA duration can correlate with a degree of severity of left ventricular dysfunction, such as during or after worsening of a congestive or chronic heart failure condition.

It is believed that sustained MA might also predict sudden cardiac arrest, such as when MA can be detected together with TWA. In an example, a combination of MA and TWA detection may better predict a risk of sudden cardiac arrest, or a risk of one or more other conditions, such as a risk of one or more other arrhythmias, as compared to TWA detection alone. For example, a combination of MA and TWA detection may improve one or more of a specificity or a sensitivity of a predictor of impending sudden cardiac arrest.

The present inventors have also recognized that physiologic information obtained from one or more sources can be used such as to automatically and better determine the MA condition, such as using information from one or more implantable sensors. In certain examples, one or more therapies can be initiated, altered, or inhibited, such as in response to the MA condition determination.

Figure 3:
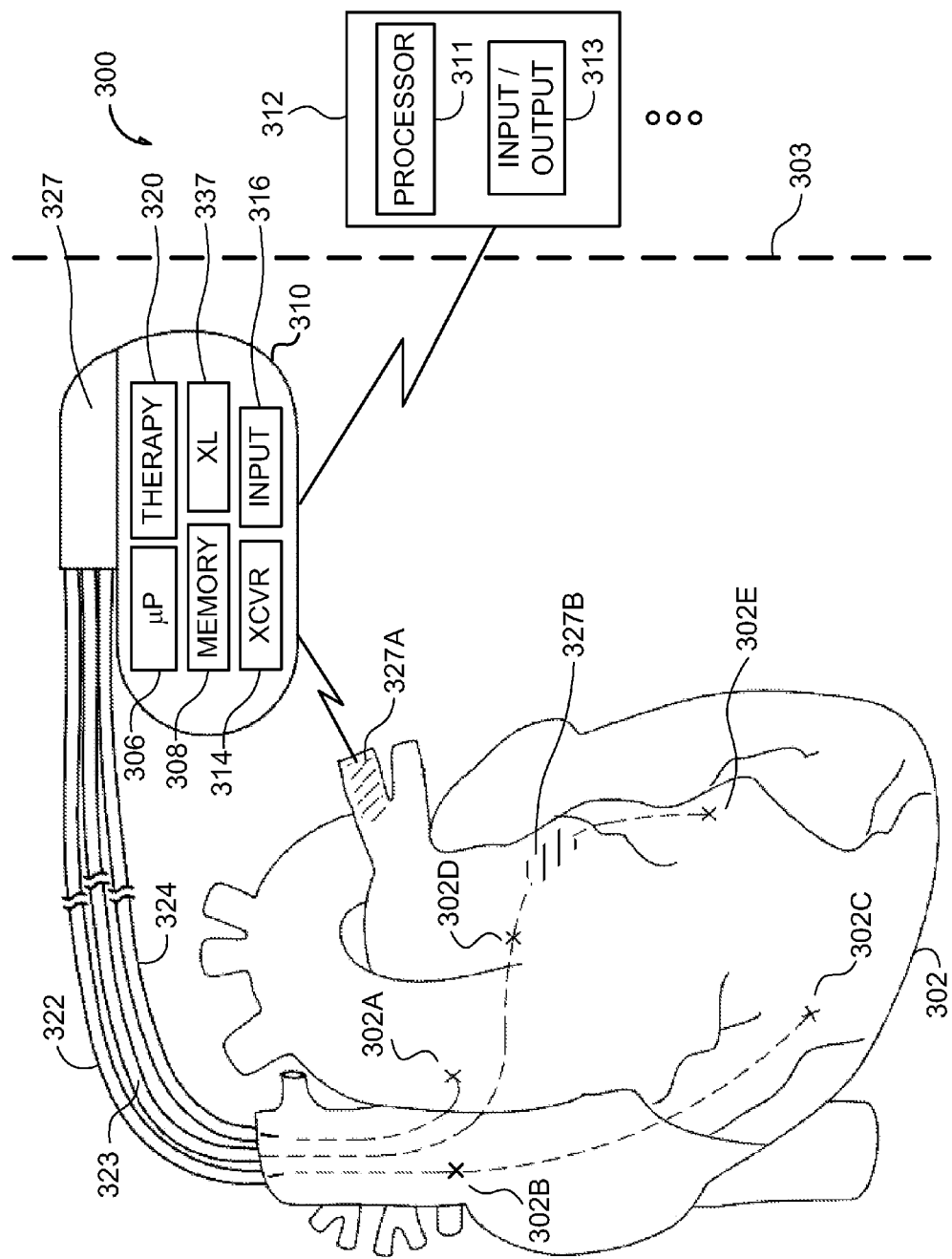
FIG. 3 illustrates generally an example of at least a portion of a system including an implantable medical device and a module external to a patient.

FIG. 1 illustrates generally an example of at least a portion of a system 100 including a cardiac mechanical alternans (MA) detector circuit 110, such as including a physiologic impedance input 115, and an intravascular pressure input 125, both coupled to a processor circuit 106, such as including one or more signal processor circuits. In an example, the detector circuit 110 can be included as a portion, part, or component of an implantable medical device, such as shown in FIG. 3. In certain examples, one or more of the impedance input 115, the processor circuit 106, or the pressure input 125 can be physically located separately from one or more ambulatory sensors, such as one or more external or implantable transducers, configured to sense a physiologic impedance or an intravascular pressure. For example, one or more of the impedance input 115 or the pressure input 125 can be configured to wirelessly or conductively receive physiologic information transmitted by the one or more sensors, such as information indicative of MA. In an example, the processor circuit 106 can determine an MA condition at least in part using physiologic information received by the impedance input 115 or the pressure input 125, such as using one or more of the methods of FIGS. 4-6.

In an example, the MA detector circuit 110 can be external to a patient, and the one or more sensors can be implanted within a patient, such as within or near a patient's heart 102 or elsewhere, such as subcutaneously or in the peripheral vasculature. In this example, information can be transferred (e.g., telemetered) from the one or more sensors such as through an inductive coupling, an electromagnetic coupling, an acoustic coupling, a conductive coupling (e.g., using body conduction), or using one or more other techniques for communication of information between the one or more sensors and the detector circuit 110.

In an example, the physiologic impedance input 115 can receive physiologic impedance information indicative of MA, such as one or more cardiac impedances measured in one or more regions of the heart 102. In an example, the intravascular pressure input 125 can receive physiologic intravascular pressure information, such as one or more intravascular pressures measured in or near one or more regions of the heart 102.

Figure 2:
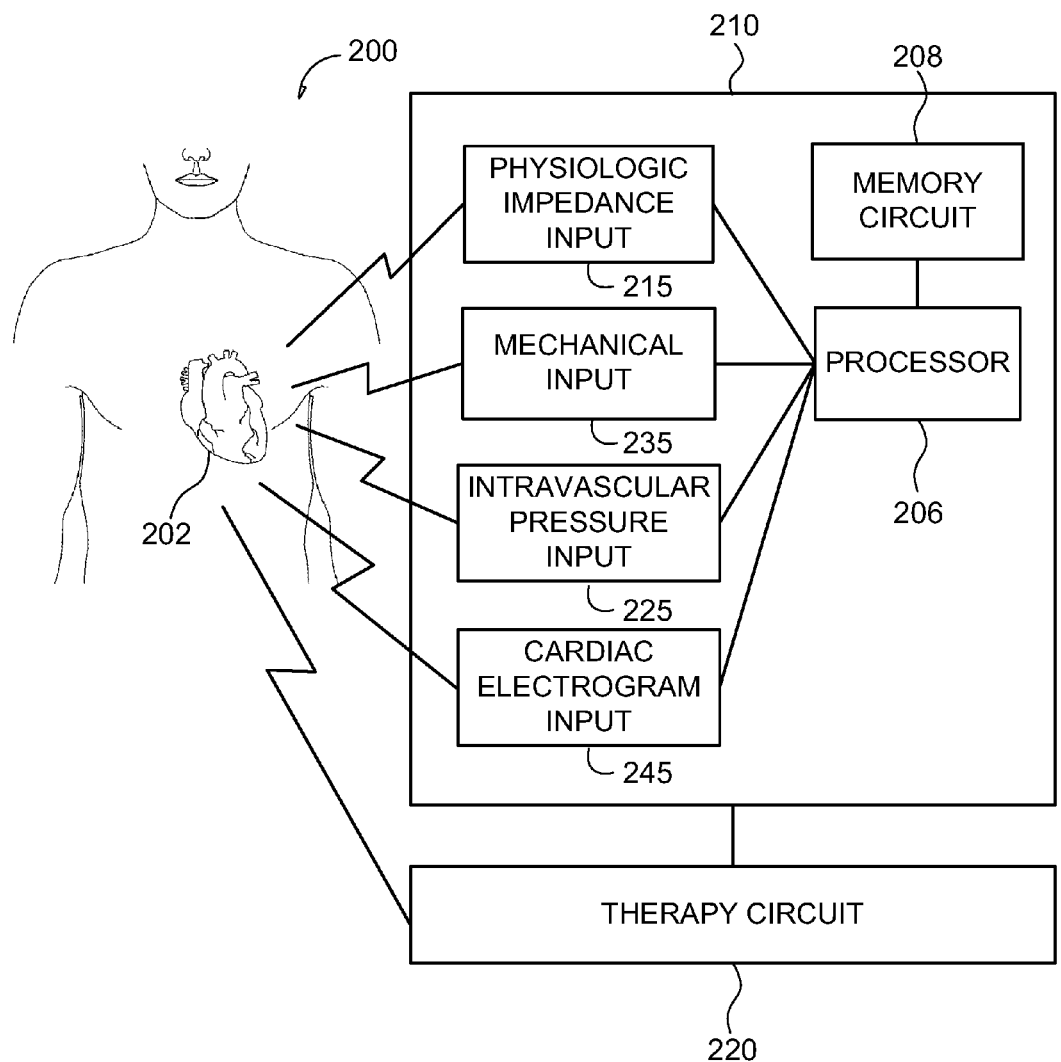
FIG. 2 illustrates generally an example of at least a portion of a system including a cardiac MA detector circuit and a therapy circuit.
Figure 4:
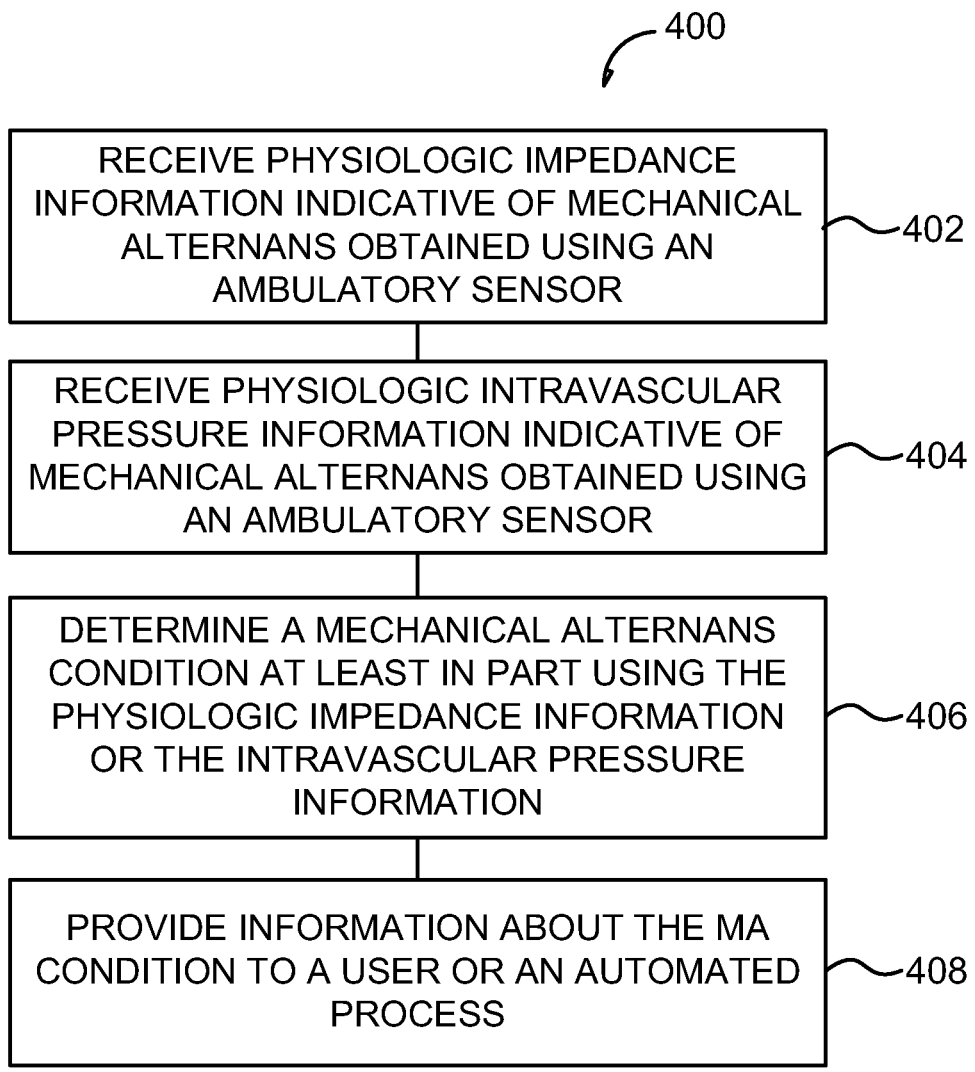
FIG. 4 illustrates generally an example of at least a portion of determining a cardiac MA condition.
Figure 5:
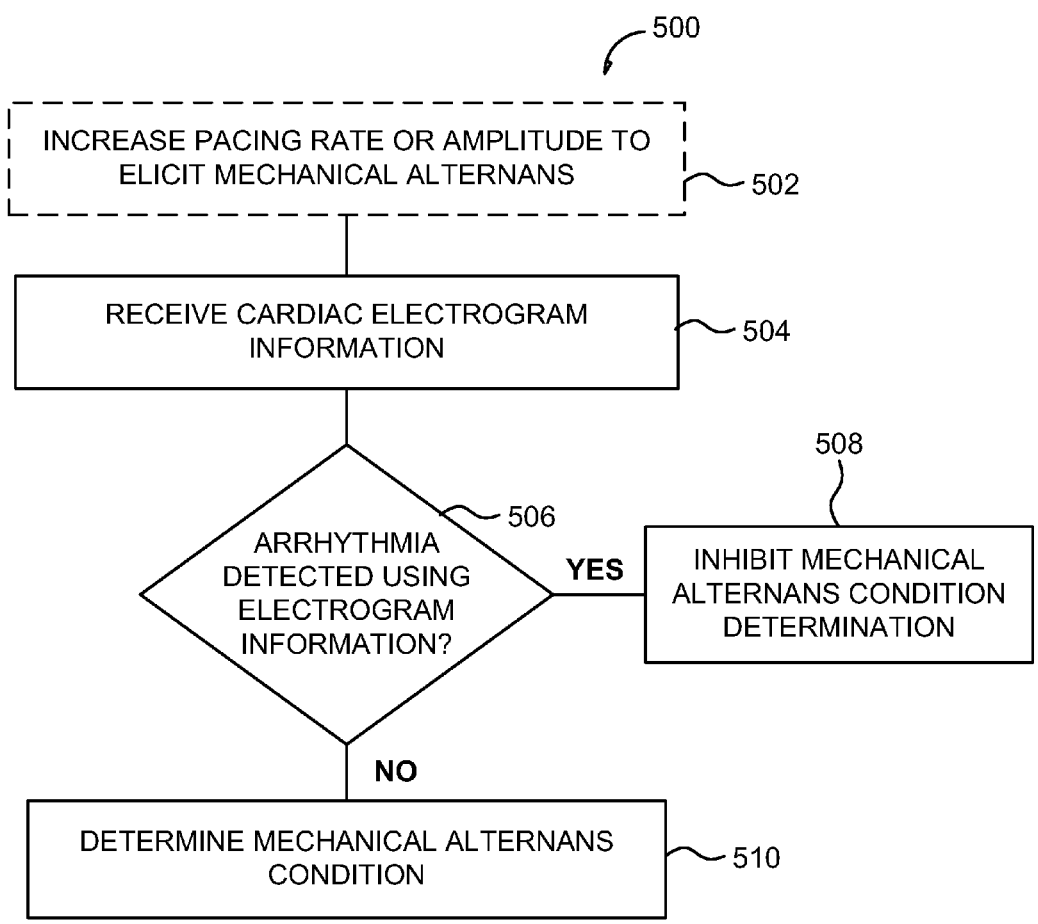
FIG. 5 illustrates generally an example including inhibiting a cardiac MA condition determination when an arrhythmia is occurring.
Figure 6:
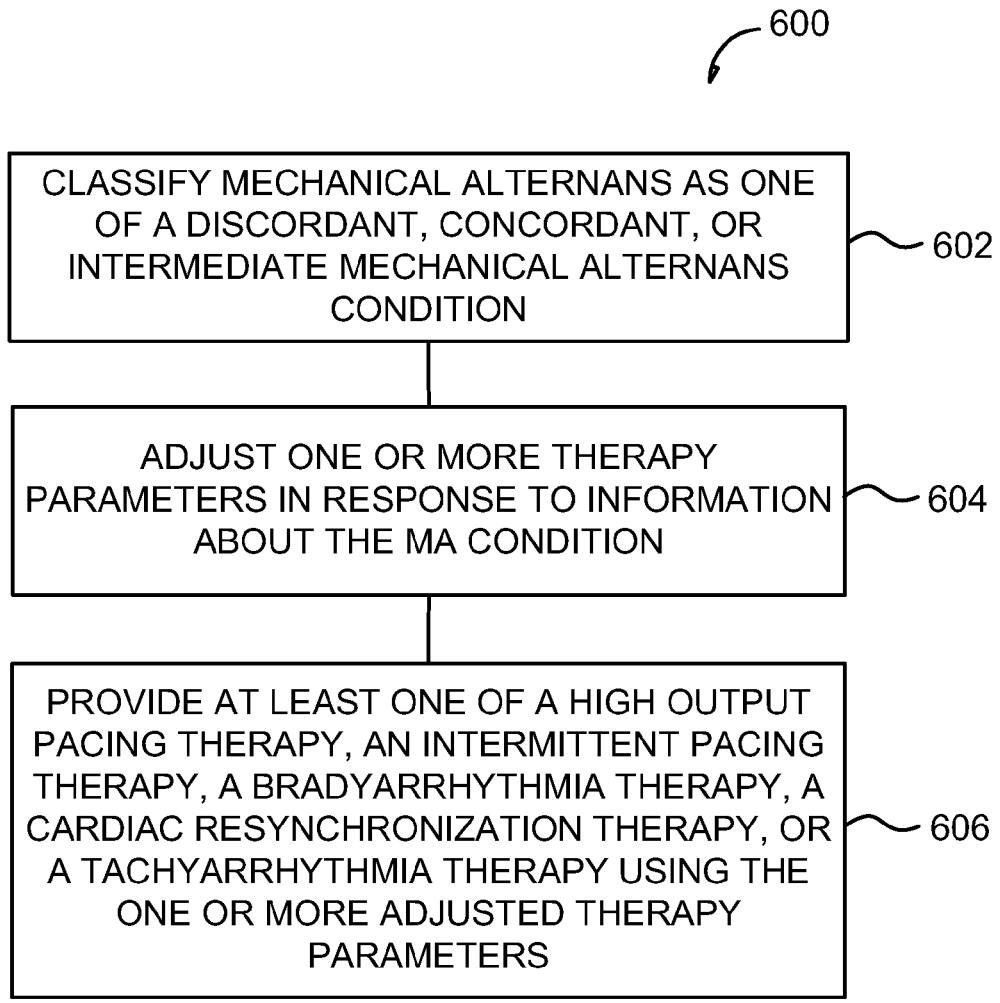
FIG. 6 illustrates generally an example of classifying a cardiac MA condition.

FIG. 2 illustrates generally an example of at least a portion of a system 200 including a cardiac MA detector circuit 210 coupled to a therapy circuit 220. In FIG. 2, the detector circuit 210 can include a physiologic impedance input 215, a mechanical input 235, an intravascular pressure input 225, and a cardiac electrogram input 245. In FIG. 2, the inputs 215, 225, 235, or 245 can be coupled to a processor circuit 206, and the inputs can be configured to provide physiologic information to the processor circuit 206, such as through one or more data buses, a wireless communication link, or a wired communication link, or using one or more other information transfer links. In certain examples, the processor circuit 206 can be configured to execute one or more instructions stored in a processor readable medium, such as a memory circuit 208. For example, the processor can determine the MA condition or perform one or more other functions, such as shown in FIGS. 4-6.

In an example, the physiologic impedance input 215 can receive physiologic impedance information, such as one or more cardiac impedances measured in one or more regions of a patient's heart 202. In an example, the intravascular pressure input 225 can receive physiologic intravascular pressure information, such as one or more intravascular pressures measured in or near one or more regions of the heart 202. In an example, the mechanical input 235 can receive physiologic cardiac vibration information indicative of MA, such as including vibration information indicative of one or more heart sounds (for example, S1, S2, S3, or S4), cardiac wall motion, blood flow, or the like. In an example, the cardiac electrogram input 245 can receive information from a cardiac electrogram sensor, such as to trigger or inhibit an MA determination by the detector circuit 210.

In an example, the physiologic information received by the cardiac electrogram input 245 can be combined with information about the MA condition, such as to identify, detect, classify, or track the progression of one or more patient conditions, such as an ischemic condition, a heart failure condition, an arrhythmic condition, an electrical alternans (e.g., TWA) condition, or an autonomic balance condition, among others.

In an example, one or more of the MA detector circuit 210 or the therapy circuit 220 can be included as a portion, part, or component of an ambulatory or implantable medical device, such as shown in FIG. 3. In other examples, the MA detector circuit 210 can be external to a patient, and one or more ambulatory sensors can be external to or implanted within a patient, such as within or near a patient's heart 202 or vasculature, or elsewhere. For example, information can be transferred (e.g., telemetered) wirelessly or otherwise from the one or more sensors such as through an inductive coupling, an electromagnetic coupling, an acoustic coupling, a conductive coupling (e.g., using body conduction), or using one or more other communicative couplings, to the respective inputs of the detector circuit 210. In an example, the therapy circuit 220 can be separate from the detector circuit 210, and the detector circuit 210 can be configured to control the therapy circuit 220 such as to alter, inhibit, or initiate a therapy, such as in response to information about the MA condition as determined by the detector circuit 210.

In an example, the therapy circuit 220 can be configured to provide one or more of a pacing therapy or an anti-tachyarrhythmia therapy, among others, to the heart 202. For example, the pacing therapy can include one or more of a bradyarrhythmia pacing therapy, a cardiac resynchronization therapy, a high-output pacing therapy, or an intermittent pacing therapy, among others. Examples of anti-tachyarrhythmia therapy can include one or more of an anti-tachyarrhythmia pacing (ATP) therapy, or a shock therapy (e.g., defibrillation or cardioversion), among others.

In an example, the high-output pacing therapy can include one or more pacing therapies as discussed in U.S. patent application Ser. No. 12/535,407, entitled "TRIGGERED HIGH OUTPUT PACING THERAPY," filed Aug. 4, 2009, which published on Feb. 25, 2010 as Publication No. 2010/0049270, assigned to Cardiac Pacemakers, Inc., which is herein incorporated by reference in its entirety, and specifically incorporating herein one or more high-output excitatory pacing therapies disclosed therein. For example, the high-output pacing (HOP) therapy can include one or more electrostimulation pulses delivered from one or multiple stimulation electrodes, such as simultaneously or with timing offsets between them. In order to adjust the stimulation parameters, the therapy circuit 220 can be configured such as to use information about the hemodynamic response of the heart 202 while the HOP is delivered from single or multiple sites such as to adjust the stimulation parameters in a manner that results in contractility improvement. In order to measure hemodynamic response, the detector circuit 210 can receive physiologic information reflective of myocardial contractility. The physiologic information can include one or more of mechanical information, intravascular pressure information, or cardiac impedance information. In an example, a HOP stimulation site or sites, a HOP amplitude of stimulation, a HOP stimulation waveform or polarity (e.g., positive, negative, bi-phasic, unbalanced, etc.), a HOP stimulation pulse duration, a number of pulses or a timing of the stimulation pulses, or the like, can be adjusted, such as using the MA determination, in order to augment contractility.

In an example, the intermittent pacing therapy can include one or more pacing therapies such as discussed in U.S. Patent Application Ser. No. 61/181,991, entitled "METHOD AND APPARATUS FOR SAFE AND EFFICIENT DELIVERY OF CARDIAC STRESS AUGMENTATION PACING," filed on May 28, 2009, and U.S. patent application Ser. No. 12/770,351, entitled "METHOD AND APPARATUS FOR SAFE AND EFFICIENT DELIVERY OF CARDIAC STRESS AUGMENTATION PACING," filed on Apr. 29, 2010 which published on Dec. 2, 2010 as Publication No. 2010/0305648, both assigned to Cardiac Pacemakers, Inc., which are incorporated herein by reference in its entirety, and specifically incorporating herein one or more cardiac stress augmentation pacing therapies disclosed therein. For example, the intermittent pacing therapy can include alternating non-pacing and pacing periods. In an example, the non-pacing periods can have a non-pacing duration during which no pacing pulse is timed to be delivered. In an example, the pacing periods each have a specified pacing duration during which pacing pulses are timed to be delivered using one or more adjusted pacing parameters, such as selected to augment cardiac stress to a level effective for slowing or stopping progression of a cardiac disorder.

FIG. 3 illustrates generally an example of at least a portion of a system including an implantable medical device 300 and a module 312 external to a patient. The implantable medical device (IMD) 310 can include one or more cardiac function management devices, such as an implantable pacemaker, an implantable cardioverter/defibrillator (ICD), a cardiac resynchronization therapy device, or one or more other implantable modules or assemblies configured to monitor or to provide therapy to a patient's heart 302. In other examples, one or more of the circuits, functions, or features of the IMD 310 can be included in an external medical device, such as a wearable patient monitor for use during ambulatory monitoring of one or more acute or chronic patient conditions.

In FIG. 3, the IMD can be coupled to one or more intravascular leads, such as an atrial lead 324, a right ventricular (RV) lead 322, or an intravascular lead configured for implant within an arterial or venous location, such as a coronary sinus (CS) lead 323. In an example, the IMD coupled wirelessly or otherwise to one or more epicardial, sub-cutaneous, or leadless electrode assemblies. In an example, the one or more leads can include multiple conductors insulated from one another, such as conductively coupled to one or more electrodes or sensors located on or within the leads. For example, the electrodes can be located in contact with or near cardiac tissue of the heart 302, such as in contact with endocardial or myocardial tissue within one or more chambers of the heart 302.

In an example, the atrial lead 324 can include one or more electrodes in a right atrial region 302A of the heart 302, such as a distal tip electrode at or near the end of the atrial lead 324. In an example, the atrial lead 324 can also include a ring electrode located near the distal tip electrode, such as to provide bipolar electrostimulation or bipolar sensing of cardiac electrical activity.

Similarly, the RV lead 322 can include one or more electrodes, such as a distal tip electrode in a right ventricular region 302C of the heart 302. In an example, the RV lead 322 can also include one or more coil or ring electrodes, such as along the length of the RV lead 322 in a superior vena cava (SVC) region 302B of the heart 302, or near the distal tip electrode of the RV lead 322. In an example, a coil electrode in the SVC region 302B, or a coil electrode near the distal tip of the RV lead 322 can be used along with the IMD 310 housing, such as for delivery of, among other therapies, pacing or anti-tachyarrhythmia therapies (e.g., shock), or for sensing cardiac electrical activity.

In an example, the CS lead 323 can include a distal tip located in a coronary vein region 302E of the heart. In an example, the CS lead 323 can include one or more electrodes between the distal tip in the coronary vein region 302E and a coronary sinus region 302D of the heart. For example, the one or more respective electrodes can provide conductive coupling between therapy or sensing circuitry in the IMD 310 and one or more respective sites the coronary vasculature, such as within or between the coronary sinus region 302D and the coronary vein region 302E.

In FIG. 3, the RV, LV, or atrial leads 322-324 can be electrically and mechanically attached to the IMD 310, such as by using a connector block 327. In an example, the connector block can provide an electrical connection between one or more circuits included in the IMD 310 and one or more electrodes associated with the leads 322-324.

In FIG. 3, the IMD 310 can include a processor, such as a microprocessor circuit 306, and a memory circuit 308 coupled to the microprocessor 306. One or more of the microprocessor 306 or the memory 308 can be coupled to various circuits included in the IMD 310, such as a transceiver circuit 314, one or more inputs such as an input 316, an accelerometer 337 or one or more other mechanical sensors (e.g., a strain gauge), or a therapy circuit 320. In an example, the therapy circuit 320 can be similar to the therapy circuit 220 discussed above in FIG. 2, and can be configured to deliver electrostimulation therapy such as to one or more sites in or near the heart 302 such as by using one or more of the RV, LV, or atrial leads 322-324.

In an example, the input 316 can include multiple physiologic information inputs, such as one or more of the intravascular pressure inputs 125, 225, the physiologic impedance inputs 115, 215, or the cardiac electrogram input 245 as discussed above in FIGS. 1-2. For example, the input 316 can include one or more circuits or blocks such as one or more amplifiers, comparators, filters, or analog-to-digital converters, such as to process or convert physiologic information received from one or more ambulatory sensors into an analog or digital format useable by the microprocessor 306 or the memory circuit 308. In an example, one or more of the input 316, microprocessor 306, memory 308, transceiver circuit 314, or accelerometer 337 can be co-integrated on or within a commonly shared integrated circuit or module, such as included as a portion of a circuit assembly included in the IMD 310.

In an example, the combination of the microprocessor 306 and one or more inputs such as the input 316 included in the IMD 310 can provide an implantable cardiac mechanical alternans (MA) detector circuit 110 or 210 as discussed above in FIGS. 1-2, such as located subcutaneously below a patient's skin 303 or muscle tissue. In this example, the IMD 310 can alter, initiate, or inhibit one or more therapies, such as provided by the therapy circuit 320, in response to an MA determination made by the microprocessor 306, such as using physiologic information indicative of MA received by the input 316.

In an example, the physiologic input 316 can include an intravascular pressure input configured to receive intravascular pressure information indicative of MA. In FIG. 3, one or more pressure sensors can be communicatively coupled to the input 316 such as a pulmonary artery pressure (PAP) sensor 327A, or a left ventricular pressure (LVP) sensor 327B such as located on or within the CS lead 323. In an example, the PAP sensor 327A can be sized and shaped to be intravascularly deliverable to an intravascular implant location, such as within a pulmonary artery.

In an example, the PAP sensor 327A can wirelessly or conductively transfer physiologic intravascular pressure information to the IMD 310, such as using an inductive coupling, an electromagnetic coupling, an acoustic coupling, a conductive coupling (e.g., using body conduction), or the like. In an example, the IMD 310 can use the transceiver circuit 314 to receive the intravascular pressure information. In an example, the transceiver 314 can then provide the intravascular pressure information to one or more of the input 316, the microprocessor 306, or the memory 308. In an example, the LVP sensor 327B can transfer physiologic intravascular pressure information to the input 316 of the IMD 310 such as using one or more respective conductors included in the LV lead 324.

In an example, the PAP sensor 327A can provide intravascular pressure information proportional to or corresponding to an RV pressure, since the PAP sensor 327A can be located near the right ventricle of the heart 302. Similarly, in an example, the LVP sensor 327B can provide intravascular pressure information proportional to or corresponding to an LV pressure, since the LVP sensor 327B can be located in the coronary vasculature near the left ventricle of the heart 302.

In an example, the PAP sensor 327A or the LVP sensor 327B can include an intravascular pressure sensor such as discussed in U.S. patent application Ser. No. 11/216,738, entitled "DEVICES AND METHODS FOR POSITIONING AND ANCHORING IMPLANTABLE SENSOR DEVICES," filed Aug. 31, 2005, which published on Jun. 8, 2006 as Publication No. 2006/0122522, assigned to Cardiac Pacemakers, Inc., which is herein incorporated by reference in its entirety, specifically incorporating an implantable pressure sensor incorporated as a portion of an implantable assembly such as an implantable lead or a stent-like anchor, the sensor configured to sense an intravascular pressure during ambulatory operation.

In an example, the LVP sensor 327B can include an intravascular pressure sensor located along an intravascular implantable lead or catheter, such as discussed in U.S. patent application Ser. No. 10/038,936, "METHOD AND APPARATUS FOR MEASURING LEFT VENTRICULAR PRESSURE," now issued as U.S. Pat. No. 6,666,826, filed on Jan. 4, 2002, assigned to Cardiac Pacemakers, Inc., which is herein incorporated by reference in its entirety, specifically incorporating an implantable pressure sensor incorporated as a portion of an implantable assembly such as an implantable lead or a stent-like anchor, the sensor configured to sense an intravascular pressure during ambulatory operation.

In an example, one or more of the electrodes, such as included on or within one or more of the respective atrial, LV, or RV leads 322-324 can be used to measure a cardiac impedance. For example, one or more cardiac impedances can be measured in a localized region of the heart. In an example, a left ventricular cardiac impedance "vector" can include a cardiac impedance measurement between a distal tip of the LV lead 324 in the coronary vein region 302E and a ring electrode on the LV lead 32 located more proximally toward the coronary sinus region 302D. Similarly, in an example, a right ventricular cardiac impedance vector can include a cardiac impedance measurement between a distal tip of the RV lead 322 located in the RV region 302C, and a ring electrode on the RV lead 322 located more proximally toward the SVC region 302B. In an example, a cross-chamber cardiac impedance can also be measured between one or more electrodes located on the left ventricular lead 323, and one or more electrodes located on the RV lead 322, the atrial lead 324, or elsewhere. In yet another example, another left ventricular cardiac impedance vector can include a cardiac impedance measurement between one or more of a distal tip of the LV lead 324 in the coronary vein region 302E, or a ring electrode on the LV lead 32 located more proximally toward the coronary sinus region 302D, and the housing of the IMD 310.

In an example, a cardiac impedance measurement can include using a pulsed current excitation signal provided across a first pair of electrodes located in a cardiac region of interest. In this example, a voltage induced by the current can then be measured across a second pair of electrodes nearby the first pair. In this example, the impedance measurement technique includes a force-current-measure-voltage (FIMV) technique. In an example, one of the current injection electrodes can be commonly shared with one of the voltage measurement electrodes, so that an impedance can be measured using three electrodes in total, rather than four. In an example, one or more bi-phasic current pulses can be used, such as at a non-excitatory energy level (e.g., the current stimulus can be below a threshold level where contraction or refractory of cardiac tissue is induced by the pulses). The bi-phasic current pulse can also provide charge neutrality such as to avoid polarization or depolarization of the tissue in the region adjacent the impedance measurement electrodes.

In an example, a synchronous current injection and voltage measurement can be used, such as discussed in relation to the physiologic impedance measurement techniques of U.S. patent application Ser. No. 12/350,728, entitled "IMPEDANCE MEASUREMENT AND DEMODULATION USING IMPLANTABLE DEVICE," filed on Jan. 8, 2009, which published on Jul. 9, 2009 as Publication No. 2009/0177110, assigned to Cardiac Pacemakers, Inc., which is herein incorporated by reference in its entirety.

In other examples, a cardiac impedance can be measured such as using a "voltage droop" technique by discharging one or more capacitors internal to the IMD 310 across two electrodes during a specified time interval, and measuring a decrease in the stored voltage on the capacitor such as during or after the discharge. In this example, the "voltage droop" technique can be used such as to measure the cardiac impedance in the region of interest using the two electrodes since the rate of discharge of the capacitor can be related to the impedance across the electrodes.

In an example, the accelerometer 337, such as a piezoelectric or microelectromechanical (MEM) sensor, can be used as a mechanical input. In this example, cardiac vibration information, such as including information about one or more heart sounds, can be mechanically coupled from the heart through body tissue or through one or more leads 322-324 to the IMD 310. In an example, the housing of the IMD 310 can mechanically vibrate corresponding to cardiac vibration, and can couple mechanical energy to the accelerometer 337. In an example, the accelerometer 337 can be used both for sensing cardiac vibration information for use in the MA determination, and for sensing the patient's movements, such as for rate modulation of pacing therapy to meet the metabolic or cardiac output demand of the patient.

In FIG. 3, the system 300 can include one or more external modules, such as an external module 312. The external module 312 can include one or more input/output modules 313, such as a user display, a keyboard, a wired or wireless transceiver circuit such as included in one or more network adapters, or one or more other input/output modules. In an example, physiologic information received by the input 316, such as one or more of physiologic impedance information, physiologic intravascular pressure information, cardiac vibration information, cardiac electrogram information, or other information can be used by an external processor 311 such as to determine a mechanical alternans condition. In an example, the external module 312 can include an implantable medical device 310 programmer, such as used by a caregiver or clinician to configure or monitor the implantable device 310, such as using a wireless coupling to the IMD 310.

In another example, the external module 312 can include a bedside, handheld, or patient-worn monitor configured to provide information to the patient or the caregiver, such as information about an MA condition. In an example, an external module 312 can communicate information about an MA condition or other information with a central server or network, either automatically or at the request of a user, such as to alert the patient or caregiver to a worsening disease status. In an example, the external module 312 can alter, inhibit, or initiate one or more therapies, such as provided by the therapy circuit 320 of the IMD 310, in response to the MA condition. In this example, the external module 312 can automatically alter, inhibit, or initiate the therapy, such as using a wireless coupling to the IMD 310, or alert the user for confirmation or instructions.

FIG. 4 illustrates generally an example of determining an MA condition. In an example, one or more portions of the example 400 can be performed by the implantable MA detector circuits 110, 210 discussed above in FIGS. 1-2, or by one or more of the IMD 310 or external module 312 discussed above in FIG. 3.

Figure 7:
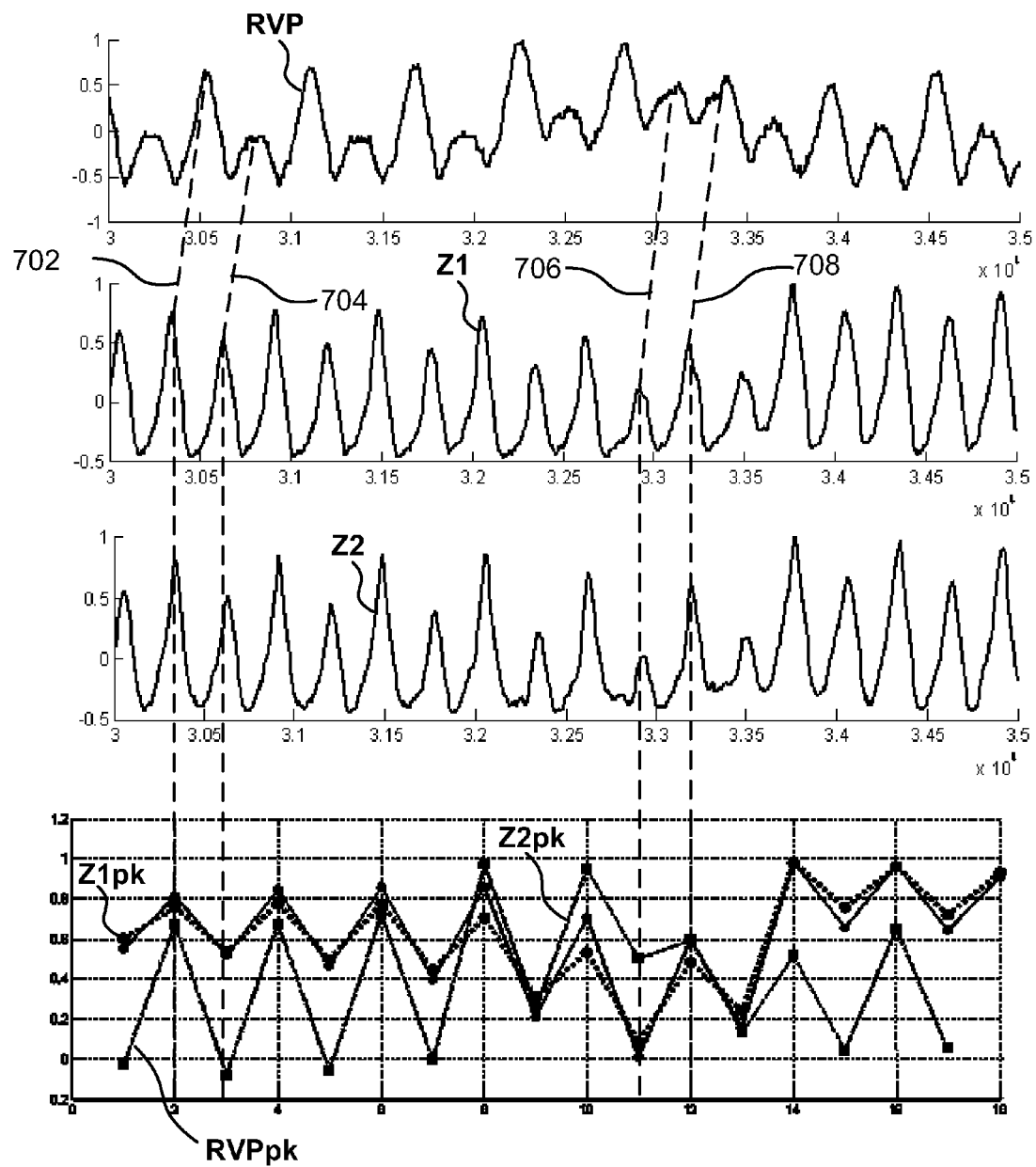
FIG. 7 includes an illustrative example of plots of physiologic information including cardiac impedance and intravascular pressure.

At 402, physiologic impedance information indicative of MA can be received. In an example, the physiologic impedance information can be received using an ambulatory sensor, such as shown above in FIG. 3. In an example, the impedance information can include a time series of instantaneously measured cardiac impedances, such as shown in FIG. 7 or 9B. At 404, physiologic intravascular pressure information indicative of MA can be received. In an example, the physiologic intravascular pressure information can be received using an ambulatory sensor, such as shown above in FIG. 3. In an example, the intravascular pressure information can include a time series of instantaneously measured pressures, such as shown in FIGS. 7, 8A, or 9C.

At 406, a mechanical alternans condition can be determined at least in part using the physiologic impedance information or the intravascular pressure information. In an example, the determining the mechanical alternans condition can include comparing information about one or more first heart contractions with information about one or more second heart contractions.

In an example, the physiologic impedance information from one or more regions of the heart can be processed, such as using one or more of the processors 106, 206, 306, or 311, or one or more inputs 115, 215, or 316 as discussed in FIGS.

1-3. In an example, the processing can include deriving an average, median, mean, or other central tendency of the cardiac impedance, such as occurring during a specified interval within the time series. In an example, the processing can include deriving a peak or minimum cardiac impedance, or a relative indication of impedance information such as a ratio of the peak impedance to the minimum impedance, such as occurring during a specified interval within the time series. In an example, the relative indication of impedance information can include a difference between a peak impedance and a minimum impedance (e.g., a "stroke" impedance).

Similarly, in an example, the physiologic intravascular pressure information from one or more regions of the heart can be processed, such as using one or more of the processors 106, 206, 306, or 311, or one or more inputs 125, 225, or 316 as discussed in FIGS. 1-3. As with the cardiac impedance above, the processing of the intravascular pressure can include deriving an average, median, mean, or other central tendency of the intravascular pressure, or deriving a peak, minimum, or relative indication of peak to minimum, etc., such as occurring during a specified interval within the time series. In an example, the processing can include deriving a relative indication of pressure information, such as a ratio or difference between a peak pressure and a minimum pressure, such as occurring during a specified interval within the time series (e.g., a "pulse pressure").

At 408, information about the MA condition can be provided, such as to a user or an automated process, such as using the external module 312 discussed above in FIG. 3.

FIG. 5 illustrates generally an example 500 of inhibiting a cardiac MA condition determination when an arrhythmia is occurring. At 504, cardiac electrogram information can be received. In an example, the cardiac electrogram information can include information about intrinsic electrical activity of the heart, such as one or more heart contractions sensed in one or more regions of the heart. In an example, the cardiac electrogram information can be sensed such as using one or more electrodes included on or within one or more intravascular leads, such as shown above in FIG. 3.

At 506, a determination whether an arrhythmia is occurring can be made, such as using the cardiac electrogram information. For example, during an arrhythmia, an MA determination might erroneously classify the arrhythmia as mechanical alternans. Thus, at 508, a mechanical alternans determination can be inhibited when an arrhythmia is detected. In an example, the one or more arrhythmias can include one or more ectopic beats, such as corresponding to bigeminy, trigeminy, a premature contraction such as one or more premature atrial contractions (PACs) or premature ventricular contractions (PVCs), etc. For example, such a when one or more premature contractions occur, the morphology of the arrhythmic beat can be different than the normal beat, confounding the MA determination. For example, the MA determination, if allowed to proceed, might mistake a variation in amplitude between impedance or pressure information corresponding to a normal beat and a PVC as indicative of MA, when no MA is actually occurring. At 510, if no arrhythmia is detected, the MA determination can proceed.

In an example, MA might not occur spontaneously at a patient's intrinsic heart rate. In this example, at 502, a pacing rate or pacing amplitude can be increased such as to achieve a specified heart rate or a specified pacing amplitude. The specified heart rate or amplitude can be selected such that in less healthy or more vulnerable patients, MA can be elicited at the specified heart rate or amplitude, while in more healthy patients or less vulnerable patients, the MA will not occur at the specified heart rate or amplitude. In an example, the accelerated pacing rate or heightened amplitude (e.g., "overdrive" pacing) can be provided when the patient is asleep, such as to avoid uncomfortable high-rate pacing while the patient is conscious. FIGS. 7 and 8A-C, below, show an illustrative example of pacing to elicit MA in a porcine model. In another example, one or more of the pacing amplitude or the pacing rate can be gradually increased, such as to search for a threshold pacing rate or pacing amplitude where MA begins to occur.

In other examples, a heart rate, morphology, or amplitude can be compared to one or more specified criteria, and the MA condition can be determined when the one or more criteria are met. For example, an MA condition determination can be triggered, such as when an intrinsic heart rate is sustained above a specified threshold heart rate for a specified duration of time. In this manner, the MA condition determination can be triggered automatically during ambulatory operation of an MA detector circuit at least in part using the cardiac electrogram information, such as included in the IMD 310 shown in FIG. 3.

FIG. 6 illustrates generally an example 600 of classifying a detected MA condition. At 602, the detected MA condition can be classified as strictly discordant, strictly concordant, or as an intermediate condition between strictly discordant and concordant. For example, physiologic information, such as one or more of cardiac vibration, intravascular pressure, or cardiac impedance information, such as obtained from different regions or portions of the heart, can be used to classify the detected MA. In an example, the MA condition can be classified as strictly concordant when MA is similarly detected in two or more regions of the heart.

For example, physiologic information can be received from a first region of the heart, such as including information corresponding to one or more relatively weaker heart contractions in the first region, and information corresponding to one or more relatively stronger heart contractions in the first region. In an example, physiologic information can be received from a second region of the heart, such as including information corresponding to one or more relatively weaker heart contractions in the second region, and information corresponding to one or more relatively stronger heart contractions in the second region.

In this example, during a specified duration, if the one or more relatively weaker heart contractions in the first region correspond to one or more relatively weaker heart contractions in the second region, and the one or more relatively stronger heart contractions in the first region correspond to one or more relatively stronger heart contractions in the second region, the MA condition can be concordant. Similarly, if there is no correspondence between respective stronger and weaker contractions in the first region and respective contractions in the second region, the MA condition can be discordant. In an example, if during a succession of observed contractions, some relatively stronger or weaker contractions in the first region correspond to some, but not all, stronger or weaker contractions in the second region, then the MA condition can be classified as an intermediate condition between concordant and discordant. In this example, the MA condition need not be strictly concordant or discordant, since the heart can exhibit differing underlying degrees of mechanical alteration between the first and second regions during the MA.

At 604, one or more therapy parameters can be adjusted in response information about the MA condition. The information about the MA condition can include whether MA is occurring, the duration of the MA, whether the MA is concordant, discordant, or intermediate. In an example, an "MA burden" can be determined, such as by determining a mean, median, average, or other central tendency of the duration of the MA condition relative to a 24 hour interval, or some other interval. In an example, a series of durations of MA conditions can be reported, such as relative to a specified interval (e.g., a day) over a series of days, weeks, months, etc. For example, a percentage of time spent in MA during the day can be stored and later reported for a series of days, such as using one or more of the IMD or the external module discussed in FIG. 3.

At 606, one or more of a high-output pacing therapy, an intermittent pacing therapy, a bradyarrhythmia therapy, a cardiac resynchronization therapy, or an anti-tachyarrhythmia therapy, can be provided such as using the one or more adjusted therapy parameters.

In an example, the therapy parameters can be adjusted or provided according to one or more of the following illustrative examples. In an illustrative example where the patient has chronic or congestive heart failure, the therapy can include cardiac resynchronization therapy (CRT), such as pacing therapy. In this example, the MA detection can include using physiologic information from two or more regions of the heart to detect concordance or non-concordance. In this example, the information can be provided by similar sensors in each region (e.g., information from respective regions includes intravascular pressure information), or by different types of sensors (e.g., cardiac impedance information from a first region, and intravascular pressure information from a second region). In this example, the first region can be a left ventricular region, and the second region can be a right ventricular region. The physiologic information can be sensed such as by using one or more sensors as discussed in FIG. 3. In an example, an alert, such as an audible alarm from an IMD 310, or a visual or audible indication from an external module 312, can be provided to the patient or caregiver to provide annunciation of the MA condition.

In this illustrative example, the adjustment can include initiating CRT pacing therapy or adjusting one or more CRT pacing parameters, such as in response to a level of concordance or discordance of the MA. The one or more pacing parameters could include a delay or offset such as between paced or sensed events in the left ventricle versus the right ventricle, an atrioventricular (AV) delay, a pacing amplitude, or a pacing vector. In this illustrative example, the adjustment could include automatically altering, initiating, or inhibiting the pacing therapy, or providing the proposed adjustment to a caregiver for confirmation or further modification by the caregiver.

In another illustrative example, the patient can have a tachyarrhythmia. In this example, the therapy can include one or more of anti-tachyarrhythmia pacing (ATP) or shock. An MA determination, such as from a single region of the heart, can be used to determine whether ATP can be used before shock, as compared to proceeding directly to shock therapy. For example, if the MA determination indicates chaotic activity and no pattern of MA can be detected, this may suggest a hemodynamically-compromising arrhythmia that warrants immediate shock without ATP.

In yet another illustrative example, the patient can be undergoing a protocol to augment cardiac stress, such as an intermittent pacing protocol as discussed above in FIG. 3. In this example, the MA detection can include using physiologic information from one or more regions of the heart such as to analyze the stress induced by the intermittent pacing protocol. In this example, one or more of the pacing parameters can be adjusted in response to the MA detection, such as a duration of time where pacing pulses will be provided versus inhibited (e.g., an intermittency), the number of pacing pulses to be delivered in sequence, the pulse width or amplitude of the pacing pulses, or the pacing site or chamber, among others.

FIG. 7 includes an illustrative example of plots of normalized physiologic information including cardiac impedance and intravascular pressure, from a porcine model paced at about 210 beats per minute, similar to the information to be obtained from a patient. In this example, one or more implantable sensors such as discussed above in FIG. 3 can be used such as to sense one or more of a right ventricular pressure, RVP, a first cardiac impedance, Z1, or a second cardiac impedance, Z2. In this illustrative example, Z1 can be a cross-chamber cardiac impedance measured between one or more electrodes in the left ventricle, and one or more electrodes in the right ventricle (e.g., an LV-RV cardiac impedance vector). Similarly, Z2 can be a cross-chamber cardiac impedance measured between the left ventricle and the right atrium (e.g., an LV-RA cardiac impedance vector). In this illustrative example, variations in the amplitude of the RVP, such as at one or more times 702 or 704 can be in-phase with one or more variations in Z1 or Z2.

In an example, one or more values can be determined from the physiologic information, such as a value corresponding to one or more relatively stronger heart contractions, such as at 702. Similarly, one or more values can be determined from the physiologic information, such as a value corresponding to one or more relatively weaker heart contractions, such as at 704. In an example, the one or more values can include a peak value, an average, mean, median or other central tendency of one or more peak values, or a relative indication of information from one or more relatively stronger beats as compared to one or more relatively weak beats. In an example, during a single contraction, a relative indication of the peak and minimum values of information measuring during the contraction can be determined, such as a ratio or difference between the peak and minimum values.

In an example, the measurement of the physiologic information or the determination of the one or more values can be triggered, such as by using information from a cardiac electrogram sensor, or using one or more other sensors. For example, a search for a maximum or a minimum of a time series of instantaneous measurements of physiologic information during a specified duration or window of time can be triggered, such as by sensing an intrinsic contraction using the cardiac electrogram sensor. In another example, one or more of an average, median, mean or other central tendency can be calculated during the specified duration or window of time. In yet another example, one or more of an energy, power, slope, sum, derivative or other determination can be made during the specified duration or window of time.

In FIG. 7, the one or more values determined from the physiologic information can include a Z1pk value, including a respective peak value corresponding to each respective contraction indicated by Z1. Similarly, Z2pk includes a respective peak value corresponding to each respective contraction indicated by Z2, and RVPpk includes a respective peak value corresponding to each respective contraction indicated by RVP. In certain example, such as shown at time 706 or 708, a variation between weaker or stronger contractions indicated by information from one sensor may not match the variation indicated by one or more other sensors. Thus, use of more than one type or "modality" of sensor, such as using both impedance and pressure sensing information as shown in FIG. 7 can provide the ability to detect MA in situations where using a single sensor modality might fail.

For example, using only pressure information might not allow detection of certain MA conditions, such as the variation in cardiac impedance between times 706 and 708, whereas using both pressure information and impedance information might allow such detection. In another example, the MA condition can be determined with greater specificity using more than one sensor modality, such as using both cardiac impedance and intravascular pressure information from a specified region of the heart, as compared to using one sensor modality individually in the specified region.

In another illustrative example, a cardiac impedance between the left ventricle and the housing of an IMD such as shown in FIG. 3 can be used as a first mode of physiologic information. In this example, a pulmonary artery pressure sensed near a right ventricle can be used as a second mode of physiologic information. Thus, physiologic information can be received from both the LV region (e.g., using the LV-housing cardiac impedance vector), and the RV region (e.g., using the PAP pressure information).

FIGS. 8A-C include illustrative examples of plots of physiologic information. The plots include a time series of instantaneous intravascular pressure information in FIG. 8A, a time series of instantaneous mechanical sensor information in FIG. 8B, and a time series of processed mechanical sensor information in FIG. 8C. The plots in FIGS. 8A-C include information derived from a porcine model paced at around 210 beats per minute, similar to the information to be obtained from a patient. In this illustrative example, FIG. 8B can include information from an accelerometer or other mechanical sensor such as discussed above in FIG. 3. In FIG. 8A, the instantaneous intravascular pressure information can include information obtained such as using one or more pressure sensors received by an intravascular pressure input, such as discussed above in FIGS. 1-3. In an example, the raw mechanical information, such as in FIG. 8B, can be processed such as to determine the timing or amplitude of one or more heart sounds, such as S1, S2, S3, or S4 heart sound, or to determine the timing or amplitude of other cardiac vibration events (e.g., wall motion, blood filling or motion, or the like). In an example, an instantaneous power, average power, or other central tendency of the power or energy corresponding to the mechanical information can be determined, such as a power of an S3 heart sound included in the mechanical information. For example, in FIG. 8C, an energy of the raw mechanical information from FIG. 8B can be determined. In an example, the energy determination can include determining an absolute value of one or more raw mechanical information samples, squaring the absolute value of each sample, and summing the group of squared absolute values, such as corresponding to a specified duration of the raw mechanical information. In an example, a power or energy determination can provide information, such as the energy shown in FIG. 8C, including mechanical alternans in-phase on a beat-to-beat basis with mechanical alternans as indicated by intravascular pressure information, such as shown in FIG. 8A.

In an example, one or more of the raw mechanical information from FIG. 8B or the energies included in FIG. 8C can be normalized, scaled, or offset, or processed using other techniques such as to more easily allow comparison between energies determined previously or energies to be determined later. In an example, a determination of an energy, a power, or other information can be triggered by one or more events such as indicated by one or more other sources of physiologic information. For example, a power determination can be triggered by an R-wave as indicated using information from a cardiac electrogram sensor, such as received by the cardiac electrogram inputs discussed in FIGS. 2-3. In this example, the power can be determined using raw mechanical information received during an interval starting at a time indicated as the peak of the R-wave, and ending such as at a time corresponding to ⅔ of the interval to the next R-wave, either paced or sensed. A power, an energy, a moving average, or one or more other determinations can be similarly made using the information provided by other sensors, such as using the pressure or impedance information discussed above in FIG. 7, such as triggered by one or more events indicated by cardiac electrogram information.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus, comprising:
a cardiac mechanical alternans (MA) detector circuit comprising:
 a physiologic impedance input configured to receive physiologic information indicative of mechanical alternans;
 an intravascular pressure input configured to receive physiologic information indicative of mechanical alternans;
 a mechanical input configured to receive physiologic cardiac vibration information indicative of mechanical alternans; and
wherein the MA detector circuit is configured to:
 detect mechanical alternans (MA) respectively from first and different second cardiac regions at least in part using the physiologic information received by the physiologic impedance input, the intravascular pressure input, and the mechanical input; and
 classify the mechanical alternans using a comparison of the detected MA from the first and second cardiac regions as one of a discordant MA condition, a concordant MA condition, or an intermediate condition between the concordant and discordant conditions.

2. The apparatus of claim 1, comprising:
a therapy circuit configured to provide at least one of a high output pacing therapy, an intermittent pacing therapy, a bradyarrhythmia therapy, a cardiac resynchronization therapy, or an anti-tachyarrhythmia therapy;
wherein the therapy circuit is configured to adjust a therapy parameter in response to the detection of the MA provided by the MA detector circuit.

3. An apparatus, comprising:
a cardiac mechanical alternans (MA) detector circuit comprising:
 a physiologic impedance input configured o receive physiologic information indicative of mechanical alternans; and
 intravascular pressure input configured to receive physiologic information indicative of mechanical alternans; and wherein the MA detector circuit is configured to:
 detect mechanical alternans (MA) respectively from first and different second cardiac regions at least in part using the physiologic information received by the physiologic impedance input and the intravascular pressure input; and
 classify the mechanical alternans using a comparison of the detected MA from the first and second cardiac regions as one of a discordant MA condition, a concordant MA condition, or an intermediate condition between the concordant and discordant conditions.

4. The apparatus of claim 3, wherein the MA detector circuit includes a mechanical input configured to receive physiologic cardiac vibration information indicative of mechanical alternans, and wherein the MA detector circuit is configured to detect the MA at least in part using the physiologic cardiac vibration information.

5. The apparatus of claim 3, comprising an intravascular pressure sensor sized and shaped to be located intravascularly within or near at least one of a pulmonary artery, a coronary sinus, or a coronary vein, and configured to provide physiologic pressure information indicative of mechanical alternans to the intravascular pressure input.

6. The apparatus of claim 3, wherein the MA detector circuit includes a cardiac electrogram input configured to receive physiologic information obtained using a cardiac electrogram sensor, and wherein the MA detector circuit is configured to determine at least one of an ischemic condition, a heart failure condition, an arrhythmic condition, an electrical alternans condition, or an autonomic balance condition using the physiologic information obtained using the cardiac electrogram sensor and the detected MA.

7. The apparatus of claim 3, comprising a therapy circuit configured to provide an electrostimulation to a heart, and wherein the MA detector circuit is configured to detect the MA at least in part using the therapy circuit to provide the electrostimulation to the heart.

8. The apparatus of claim 7, wherein the therapy circuit is configured to increase, in response to a command, at least one of a pacing amplitude or a pacing rate beyond a respective specified baseline pacing amplitude or a specified baseline pacing rate, and wherein the MA detector circuit is configured to detect the MA at least in part using at least one of the pacing amplitude increase or the pacing rate increase.

9. apparatus of claim 3, wherein the MA detector circuit includes a cardiac electrogram input configured to receive physiologic information obtained using an cardiac electrogram sensor, and wherein the MA detector circuit is configured to at least one of inhibit or trigger the mechanical alternans detection using the physiologic information obtained using the electrogram sensor.

10. The apparatus of claim 9, wherein the physiologic information includes an intrinsic heart rate, and wherein the MA detector circuit is configured to detect the MA at least in part during an interval when the intrinsic heart rate exceeds a specified threshold.

11. The apparatus of claim 3, comprising:
a therapy circuit configured to provide at least one of a high output pacing therapy, an intermittent pacing therapy, a bradyarrhythmia therapy, a cardiac resynchronization therapy, or an anti tachyarrhythmia therapy;
wherein the therapy circuit is configured to adjust a therapy parameter in response to information about the MA condition provided by the MA detector circuit.

* * * * *